United States Patent [19]
Buchel et al.

[11] 3,983,240
[45] Sept. 28, 1976

[54] COMPOSITIONS AND METHOD FOR TREATING MYCOSES

[75] Inventors: Karl Heinz Buchel; Manfred Plempel; Wolfgang Kramer, all of Wuppertal, Germany

[73] Assignee: Bayer Aktiengesellschaft, Germany

[22] Filed: Sept. 9, 1974

[21] Appl. No.: 504,429

[30] Foreign Application Priority Data
Sept. 19, 1973 Germany............................ 2347057

[52] U.S. Cl. ............................................... 424/269
[51] Int. Cl.² ........................................... A61K 31/41
[58] Field of Search ..................................... 424/269

[56] References Cited
UNITED STATES PATENTS
3,812,142 5/1974 Buchel et al........................ 424/269

*Primary Examiner*—Jerome D. Goldberg

[57] ABSTRACT

Antimicrobial compositions comprising 1-(1,2,4-triazolyl-1')-2-phenoxy alkane derivatives as the active ingredient.

The compositions are well tolerated and combine their non-toxic effect within an especially good antimycotic activity.

43 Claims, No Drawings

COMPOSITIONS AND METHOD FOR TREATING MYCOSES

This invention relates to pharmaceutical compositins containing various 1-(1,2,4-triazolyl-1')-2-phenoxy alkane derivatives as the active ingredient and to their use as antimicrobial agents.

Specifically, the antimicrobial compositions of this invention comprise as the active ingredient a compound of the formula:

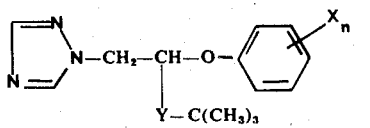

(I)

or the non-toxic pharmacologically acceptable salts thereof; wherein:
X is hydrogen, halo, polyhaloalkyl, alkyl, alkoxy, alkylthio, alkylsulfonyl, nitro, cyano, carbalkoxy, phenyl or substituted phenyl in which the benzene nucleus contains from 1 to 3 of the same or different radicals selected from lower alkyl, nitro or halo;
$n$ is 0 or an integer having a value of 1 to 5; and
Y is a keto group or a functional derivative thereof, preferably carbonyl, oximo, hydrazono or a ketal of the formula —$C(OR)_2$—wherein
R is hydrogen or alkyl;
in combination with a non-toxic pharmaceutically acceptable carrier.

In the above formula (I) when X is halo, it is preferably fluoro, chloro, or bromo; polyhaloalkyl may contain 1 or 2 carbon atoms and 2 to 5 moieties, preferably chloro or fluoro as illustrated by trifluoromethyl; the straight or branched chain alkyl contains from 1 to 4 carbon atoms and includes, for example, methyl, ethyl, n-propyl, isopropyl and tert.-butyl; alkoxy and alkylthio contain from 1 to 4 carbon atoms as illustrated by methoxy, ethoxy, n-propoxy, n-butoxy, methylthio, ethylthio and n-propylthio and the like; alkylsulfonyl contains 1 to 4 carbon atoms, preferably 1 or 2 carbon atoms as, for example, methylsulfonyl and ethylsulfonyl; carbalkoxy contains from 1 to 4 carbon atoms and includes, for example, methoxycarbonyl and ethoxycarbonyl; nuclear substituted phenyl containing from 1 to 3 of the same or different substituents includes such nuclear substituents as halo, for example, chloro, fluoro or bromo; in addition the nuclear substituents include nitro or lower alkyl such as methyl or ethyl and the like. Also, in the ketal group —$C(OR)_2$— where R is hydrogen or alkyl, the latter includes alkyl or 1 to 4 carbon atoms, preferably methyl or ethyl.

These compositions exhibit strong antimicrobial activity and are especially useful as antimycotic agents. The 1-(1,2,4-triazolyl-1')-2-phenoxy alkane derivatives of this invention and the non-toxic pharmacologically acceptable salts are well tolerated by the body system and, therefore, they are especially well suited for antimicrobial use. Also, the instant compounds (I) exhibit an especially outstanding antimycotic activity. The compounds may be employed per se, that is, as the free base or in the form of their non-toxic pharmacologically acceptable salts and throughout this specification when salts are referred to, it is to be understood that they embrace only the pharmacologically acceptable salt derivatives.

One embodiment of this invention relates to antimicrobial compositions in which the active ingredient is a compound of the formula (I) wherein:
X is hydrogen, halo, lower alkyl or nitro;
$n$ is 0 or an integer having a value of 1 to 3; and
Y is carbonyl or ketal of the formula —$C(OR)_2$— wherein
R is hydrogen or alkyl of 1 or 2 carbon atoms.

A second embodiment of this invention relates to antimicrobial compositions in which the active ingredient is a compound of the formula (I) wherein:
X is halo, polyhaloalkyl of 1 or 2 carbon atoms and containing 2 to 5 halo moieties, alkoxy of 1 to 4 carbon atoms, alkylthio of 1 to 4 carbon atoms, alkylsulfonyl of 1 to 4 carbon atoms, nitro, cyano, carbalkoxy of 1 to 4 carbon atoms, or phenyl;
$n$ is 0 or an integer having a value of 1 to 3; and
Y is carbonyl, or a ketal of the formula —$C(OR)_2$-. wherein
R is hydrogen or alkyl of 1 to 4 carbon atoms;
and the non-toxic pharmacologically acceptable salts thereof.

Still another embodiment of this invention relates to antimicrobial compositions in which the active ingredient is a compound of the formula:

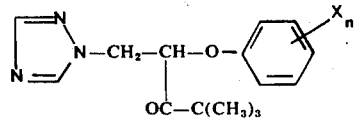

wherein:
X is hydrogen, chloro, bromo, fluoro, methyl or nitro; and
$n$ is 0 or an integer having a value of 1 or 2;
and the non-toxic pharmacologically acceptable salts thereof.

A preferred embodiment of this invention includes those compositions in which the active ingredient is a compound of the formula (Ia):

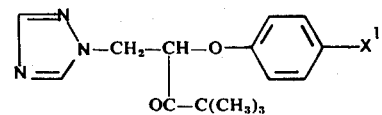

II wherein:
$X^1$ is halo, preferably fluoro, chloro or bromo;
and the non-toxic pharmacologically acceptable salts thereof, preferably the hydrohalic acid salts such as the hydrochloride or hydrobromide.

An especially preferred embodiment of this invention comprises those compositions wherein the active ingredient corresponds to formula (II) above, wherein $X^1$ is fluoro, chloro or bromo, and the hydrohalic acid salts thereof.

The above described (1-(1,2,4-triazolyl-1')-2-phenoxy alkanes (I) form salts with all of the various acids which are usually employed in preparing pharmaceutical products. Suitable acids include, for example, the hydrogen halide acids as, for example, hydrochloric and hydrobromic acid, preferably hydrochloric acid; phosphoric acid, nitric acid and various mono- and dicarboxylic acids and hydroxy substituted carboxylic acids as, for example, acetic acid, maleic acid, succinic acid, fumaric acid, tartaric acid, citric acid, salicylic acid, sorbic acid and lactic acid; and naphthalenedisulfonic acid.

Illustrative of the active ingredients (I) of this invention are the following compounds:

1-(1,2,4-triazolyl-1')-2-phenoxy-4,4-dimethyl-pentan-3-one, 1-(1,2,4-triazolyl-1')-2-(4-chlorophenoxy)-4,4-dimethyl-pentan-3-one, 1-(1,2,4-triazolyl-1')-2-(4-fluorophenoxy)-4,4-dimethyl-pentan-3-one, 1-(1,2,4-triazolyl-1')-2-(4-bromophenoxy)-4,4-dimethyl-pentan-3-one, 1-(1,2,4-triazolyl-1')-2-(2,4-dichlorophenoxy)-4,4-dimethyl-pentan-3-one, 1-(1,2,4-triazolyl-1')-2,4,5-trichlorophenoxy)-4,4-dimethyl-pentan-3-one, 1-(1,2,4-triazolyl-1')-2-(4-nitrophenoxy)-4,4-dimethyl-pentan-3-one, 1-(1,2,4-triazolyl-1')-2-(2-chlorophenoxy)-4,4-dimethyl-pentan-3-one, 1-(1,2,4-triazolyl-1')-2-(3-chlorophenoxy)-4,4-dimethyl-pentan-3-one and 1-(1,2,4-triazolyl-1')-2-(2,3-dimethylphenoxy)-4,4-dimethyl-pentan-3-one.

The compounds employed as the active ingredients (I) and the compositions of this invention can be prepared from known starting materials in accordance with conventional methods. One such process comprises treating a triazole with a compound of the formula:

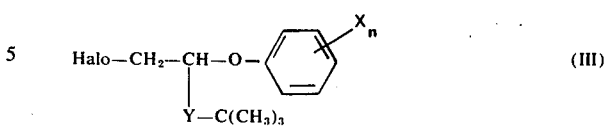

wherein
X, Y and $n$ are as defined above; and
"Halo" is a halo moiety, preferably, chloro or bromo.

The reaction is preferably carried out in acetone or acetonitrile with 1 to 1.5 mols of potassium carbonate or excess triazole (a total of 2 to 2.1 mols) as acid-binding agents, at temperatures between 80° and 120°C. To isolate the desired compounds of the invention the precipitate is filtered off and rinsed with solvent and the filtrate is freed from the solvent under reduced pressure. The residue is extracted with water and methylene chloride, the organic phase is dried and the solvent is distilled off under reduced pressure. The oily residue crystallizes on trituration or is purified further, if appropriate by distillation or salt formation.

The starting materials identified by formula (III) in the preceding paragraph can be prepared by treating a suitable phenoxy substituted alkanone (IV, infra) with formaldehyde or para-formaldehyde in the presence of a suitable base such as alkali, preferably, in an inert organic solvent as, for example, in ethanol. The reaction is conducted at elevated temperatures as, for example, at reflux temperatures and the resulting hydroxymethyl substituted intermediate (V) is then halogenated as, for example, with thionyl chloride in an inert polar organic solvent such as methylene chloride at room temperature to afford the desired compound:

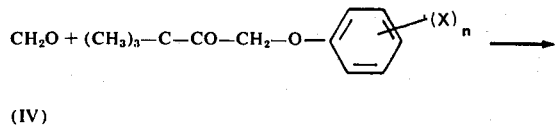

(IV)

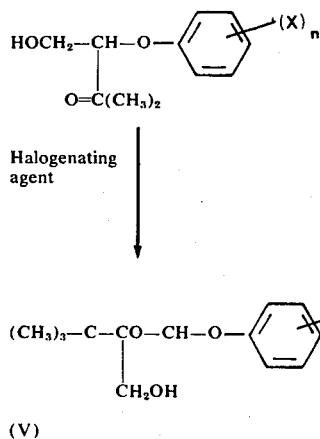

(V)

wherein
X and $n$ are as defined above.

The resulting compound (V) may then be isolated by conventional means and, if desired, the keto moiety can be converted by generally known procedures to the corresponding oximino, hydrazono or acetyl counterpart.

The phenoxy substituted alkanones of formula IV (supra) are known from German Offenlegungsschrift (German Published Specification) No. 2,105,490 or can be prepared in accordance with generally known methods.

The 1-(1,2,4-triazolyl-1')-2-phenoxy alkane compounds which are employed as the active ingredients in the instant compositions form salts with acids according to conventional means as, for example, by simply combining the active ingredient in ether or petroleum ether, followed by the addition of the appropriate acid.

The compounds of the invention exhibit antimicrobial, especially strong antimycotic, effects. They possess a very broad antimycotic spectrum of action, especially against dermatophytes and blastomyces as well as bi-phase fungi, for example against species of Candida (such as *Candida albicans*), species of Epidermophyton (such as *Epidermophyton floccosum*), species of Aspergillus (such as *Aspergillus fumigatus* and niger), species of Trichophyton (such as *Trichophyton mentagrophytes*), species of Microsporon (such as *Miscrosporon felineum*), species of Penicillium (such as *Penicillium commune*), and *Sporotrichum schenckii*, *Histoplasma capsulatum* and *Coccodioides immitis*. The last three species are representative of the bi-phase fungi. This list of species in no way represents a limitation of the microbes which can be combated and is only illustrative in character.

The following may be mentioned as examples of fields of indication in human medicine:

Dermatomycoses and systemic mycoses caused by *Trichophyton mentagrophytes* and other species of Trichophyton, species of Microsporon, *Epidermophyton floccosum*, blastomyces and bi-phase fungi as well as moulds.

The following may be mentioned as examples of fields of indication in veterinary medicine:

All dematomycoses and systemic mycoses, especially those caused by the above-mentioned pathogens.

The good antimicrobial activity of the compounds of the invention can be demonstrated by the following in vitro and in vivo experiments.

1. DETERMINATION OF THE ANTIMYCOTIC ACTIVITY IN VITRO

Description of the experiment:

The nutrient substrate used as Sabourauds' milieu d'epreuve. The incubation temperature was 28°C and the incubation time was 24 to 96 hours. *Candida albicans* and *Trichophyton mentagrophytes* were employed as the test pathogens. The tests were carried out with an active compound concentration of 1,10 to 100 λ/ml of nutrient medium.

The test results showed that the compounds of Examples 2, 3, 4, 8, 9, 10, 11, 12 and 13 without added serum completely inhibit the growth of the pathogens in concentrations up to 10 mcg/mg

2. DETERMINATION OF THE ANTIMYCOTIC ACTIVITY IN VIVO IN CANDIDOSIS OF MICE.

Description of the experiment:

Mice of the type $SPF-CF_1$ were infected intravenously with $1-2 \times 10^6$ logarithmically growing Candida cells suspended in physiological sodium chloride solution. One hour before infection and seven hours after infection the animals were treated orally with 100 mg of the preparations/kg of body weight.

Untreated animals died of the infection 3 to 6 days after infection. The survival rate on the 6th day after infection was about 5% in the case of untreated control animals.

It was found that the compound from Example 13 had the best action. On the 6th day after infection, 160 out of 200 animals (80%) survived.

As stated above, the invention relates to the use in human and veterinary medicine of the compounds of the invention.

The pharmaceutical compositions of the present invention contain a major or minor amount e.g. 99.5% to 0.1%, preferably 95% to 0.5% of at least one 1,2,4-triazole as above defined in combination with a pharmaceutically acceptable non-toxic, inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from about 10 to 300 mg/kg of body weight of the active ingredient and preferably 50 to 200 mg/kg of body weight per day. In some instances a sufficient therapeutic effect can be obtained at a lower dose while in others, a larger dose will be required.

The preferred daily dose for administration of the medicaments of the invention is from about 0.5 to 30 g., especially 2.5–20 g., of active ingredient.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tables are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The following Examples A to D describe by way of illustration only the preparation of typical pharmaceutical compositions and medicaments in dosage unit form according to the invention.

EXAMPLE A: 1% STRENGTH SOLUTION FOR TOPICAL TREATMENT

Sufficient polyethylene glycol 400 is added to 1 g of the compound of the invention described in Example 4, while stirring and warming gently, to produce a total of 100 g of solution.

EXAMPLE B: 1% STRENGTH OINTMENT FOR TOPICAL TREATMENT 1 g of the product of Example 4 is triturated with 5 g of viscous medicinal paraffin. Thereafter, sufficient ointment base consisting of medicinal paraffin and polyethylene is added to produce a total of 100 g of ointment.

EXAMPLE C: 10% STRENGTH SUSPENSION ELIXIR FOR ORAL ADMINISTRATION

Sufficient vegetable oil is added to a mixture of 10 g of the product of Example 2, 0.05 g of sodium saccharin, 2 g of colloidal silica and 0.2 g of peppermint oil to produce a total of 100 g of suspension elixir.

EXAMPLE D: TABLETS CONTAINING 200 MG OF ACTIVE COMPOUND FOR ORAL ADMINISTRATION 2 g of the product of Example 4, 1 g of lactose and 0.3 g of maize starch are granulated with 0.1 g of maize starch paste. The mixture is beaten through a sieve of approximately 4 to 6 mm mesh width and dried. This dried mixture is homogenized through a sieve of 0.8 to 1 mm mesh width and then mixed with 0.15 g of starch and 0.02 g of magnesium stearate. The mixture thus obtained is pressed to give 10 tablets.

The remaining compounds of the invention can be made up as illustrated above into pharmaceutical compositions and medicaments in dosage unit form according to the invention.

The following examples illustrate the method by which the active ingredients of this invention may be prepared for use in the instant compositions.

EXAMPLE 1

1-(1,2,4-Triazolyl-1')-2-Phenoxy-4,4-Dimethyl-Pentan-3-One

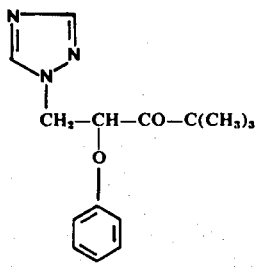

CH$_2$—CH—CO—C(CH$_3$)$_3$

Step A: 1-Chloro-2-Phenoxy-4,4-Dimethyl-Pentan-3-One

1-Hydroxy-2-phenoxy-4,4-dimethyl-pentan-3-one (111.1 g, 0.5 mol) is dissolved in 500 ml of methylene chloride. Thionyl chloride (62 g, 0.52 mol) is added dropwise to the solution at room temperature. The start of the reaction can be accelerated by gentle warming. After a reaction time of two hours at room temperature, the solvent is distilled off in vacuo and the oily residue is degassed in a high vaccum to afford 93.0 g (77% of theory) of 1-chloro-4,4-dimethyl-2-phenoxy-pentan-3-one as an oil having a refractive index of $n_D^{20}$ = 1.5081 and a boiling point of (0.4 mm Hg)/110°C.

Step B: 1-Hydroxy-2-Phenoxy-4,4-Dimethyl-Pentan-3-One

1-Phenoxy-3,3-dimethyl-butan-2-one (192.2 g, 1.0 mol) prepared according to German Offenlegungsschrift, i.e., (German Published Specification No. 2,105,490; Example 3) and having a boiling point of 75°-83°C at 0.08 atmospheres is dissolved in ethanol (800 ml) and a 30% formaldehyde solution (240 ml, 2.4 mols) is added. A 10% sodium hydroxide solution (5 ml) is then added until the pH is 9. The reaction mixture is heated for 4 hours reflux and the solvent is distilled off in vacuo. The resulting precipitate is filtered off, well rinsed with petroleum ether and discarded. The filtrate is freed from the solvent in vacuo and the resulting oil is taken up in ether and extracted by shaking with water. The organic phase is dried over sodium sulphate and freed from the solvent and the residue is purified by vaccum distillation to afford 145 g (65% of theory) of 1 -hydroxy-2-phenoxy-4,4-dimethyl-pentan-3-one, boiling point 95°–100°C (0.1 mm Hg).

Step C: 1-(1,2,4-Triazolyl-1')-2-Phenoxy-4,4-Dimethyl-Pentan-3-One

1-Chloro-4,4-dimethyl-2-phenoxy-pentan-3-one (24 g, 0.1 mol) dissolved in anhydrous acetone (50 ml) is slowly added dropwise to a suspension of potassium carbonate (13.8 g, 0.1 mol) and 1,2,4-triazole (13.8 g, 0.2 mol) in anhydrous acetone (400 ml) while boiling and stirring under a reflux condenser. The reaction is complete after 17 hours stirring at the boil under reflux.

After cooling, the precipitate is filtered off, rinsed well with anhydrous acetone and the precipitate is discarded. The filtrate is freed from the solvent in vacuo. The oily residue is taken up in methylene chloride and repeatedly extracted by shaking with water. The organic phase is dried over sodium sulphate and the solvent is distilled off in vacuo. The resulting oil crystallizes after trituration with pentane to afford 19.5 g (71% of theory) of 1-(1,2,4-triazolyl-1')-2-phenoxy-4,4-dimethyl-pentan-3-one having a melting point of 56°-58°C.

By following the procedure in Example 1, all of the 1-(1,2,4-triazolyl-1')-2-phenoxy-4,4-dimethyl-pentan-3-ones (I) of this invention may be obtained. The following equation illustrates the procedure of Example 1, steps A, B and C, and together with Table I illustrate the starting materials which may be employed in the said process and the final products obtained thereby:

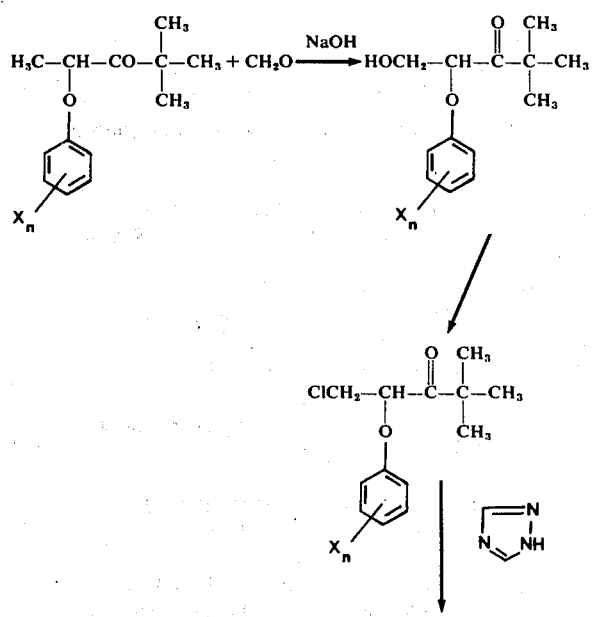

-continued

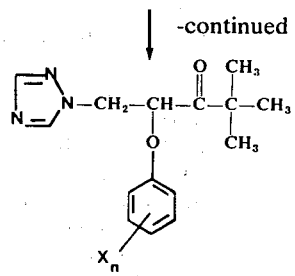

TABLE I

| Example No. | X | n | Melting point °C |
|---|---|---|---|
| 2 | 4-Cl | 1 | 55–57 |
| 3 | 2,4-Cl₂ | 2 | 75–77 |
| 4 | 4-Br | 1 | 56–58 |
| 5 | 4-CH₃ | 1 | 42–44 |
| 6 | 2,4-(CH₃)₂ | 2 | 62–64 |
| 7 | 3,4-(CH₃)₂ | 2 | 65 |
| 8 | 2,3-(CH₃)₂ | 2 | 47–48.5 |
| 9 | 2-CH₃ 4-Cl | 2 | 63–65 |
| 10 | 2,5-Cl₂ | 2 | 78–79.5 |
| 11 | 3-Cl | 1 | 73.5–74 |
| 12 | 2-Cl | 1 | 67–68.5 |
| 13 | 4-F | 1 | 71–72 |
| 14 | 4-NO₂ | 1 | 97–98 |

What is claimed is:

1. A pharmaceutical composition useful for treating mycoses in humans and animals which comprises an antimycotically effective amount of a compound of the formula:

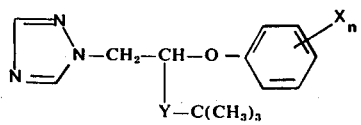

or a pharmaceutically acceptable non-toxic salt thereof wherein
  X is halo;
  n is 0 or an integer having a value of 1 to 5; and
  Y is carbonyl or a ketal of the formula —C(OR)₂— wherein
  R is hydrogen or lower alkyl;
in combination with a pharmaceutically acceptable non-toxic inert diluent or carrier.

2. A composition according to claim 1 wherein
  n is 0 or an integer having a value of 1 to 3; and
  Y is carbonyl or a ketal of the formula —C(OR)₂— wherein
  R is hydrogen or alkyl of 1 or 2 carbon atoms.

3. A composition according to claim 1 wherein
  n is 0 or an integer having a value of 1 to 3; and
  Y is carbonyl, or a ketal of the formula —C(OR)₂— wherein R is hydrogen or alkyl of 1 to 4 carbon atoms.

4. A composition according to claim 1 wherein the active ingredient is a compound of the formula:

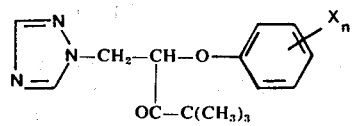

or a pharmaceutically acceptable non-toxic salt thereof wherein
  X is chloro, bromo or fluoro; and
  n is 0 or an integer having a value of 1 or 2.

5. A composition according to claim 1 wherein the active ingredient is a compound of the formula:

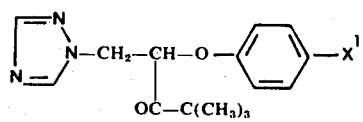

or a pharmaceutically acceptable non-toxic acid addition salt thereof wherein
  X¹ is fluoro, chloro or bromo.

6. A composition according to claim 1 wherein the active ingredient is a compound of the formula:

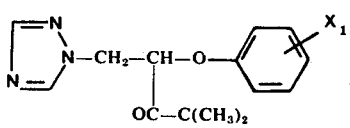

or a pharmaceutically acceptable non-toxic hydrohalic acid salt thereof wherein
  X¹ fluoro, chloro or bromo.

7. A composition according to claim 1 wherein the active ingredient is:

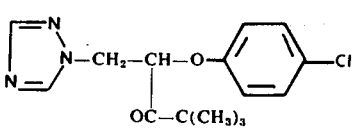

8. A composition according to claim 1 wherein the active ingredient is:

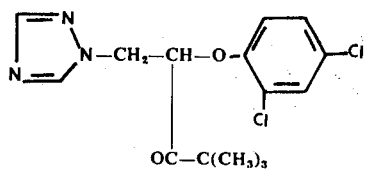

9. A composition according to claim 1 wherein the active ingredient is:

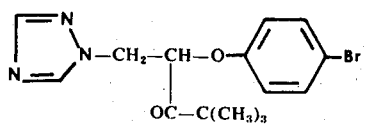

10. A composition according to claim 1 wherein the active ingredient is:

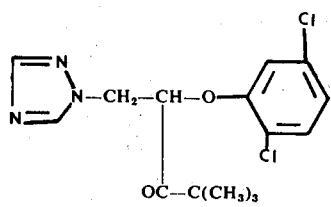

11. A composition according to claim 1 wherein the active ingredient is:

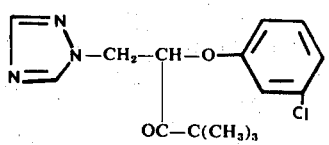

12. A composition according to claim 1 wherein the active ingredient is:

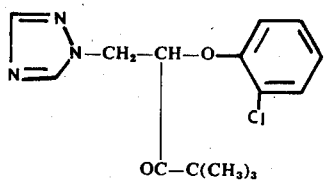

13. A composition according to claim 1 wherein the active ingredient is:

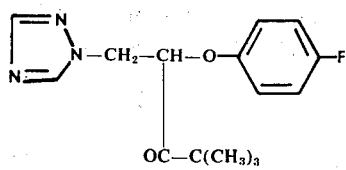

14. A composition according to claim 1 wherein the active ingredient is:

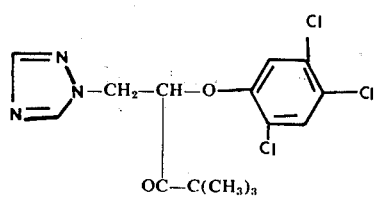

15. A composition according to claim 1 wherein Y is carbonyl.

16. A composition according to claim 1 wherein the compound is in the form of a salt selected from the group consisting of the hydrochloride, hydrobromide, phosphate, nitrate, acetate, maleate, succinate, fumarate, tartrate, citrate, salicylate, sorbate, lactate and naphthalene disulphonate.

17. A composition according to claim 16 wherein the salt is the hydrochloride.

18. A composition according to claim 1 in oral administration form.

19. A composition according to claim 1 in parenteral administration form.

20. A composition according to claim 1 in topical application form.

21. A method for treating mycotic infections in humans and animals which comprises administering to a human or animal in need thereof an antimycotically effective amount of an antimycotic composition comprising an antimycotically effective amount of a compound of the formula:

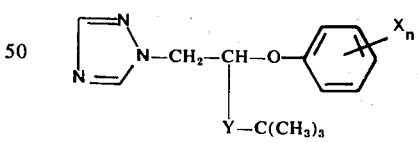

or a pharmaceutically acceptable non-toxic salt thereof wherein
X is halo;
$n$ is 0 or an integer having a value of 1 to 5; and
Y is carbonyl or a ketal of the formula $-C(OR)_2-$ wherein
R is hydrogen or lower alkyl;
in combination with a pharmaceutically acceptable non-toxic inert diluent or carrier.

22. A method according to claim 21 wherein Y is carbonyl.

23. A method according to claim 21, wherein
$n$ is 0 or an integer having a value of 1 to 3; and Y is carbonyl, or a ketal of the formula —C(OR)$_2$—
wherein R is hydrogen or alkyl of 1 or 2 carbon atoms.

24. A method according to claim 21 wherein
  $n$ is 0 or an integer having a value of 1 to 3; and
  Y is carbonyl, or a ketal of the formula —C(OR)$_2$—
  wherein
  R is hydrogen or alkyl of 1 to 4 carbon atoms.

25. A method according to claim 21, wherein the active ingredient is a compound of the formula:

[Structure: triazole-N—CH$_2$—CH(OC—C(CH$_3$)$_3$)—O—phenyl-X$_n$]

or a pharmaceutically acceptable non-toxic salt thereof wherein
  X is chloro, bromo or fluoro; and
  $n$ is 0 or an integer having a value of 1 or 2.

26. A method according to claim 21, wherein the active ingredient is a compound of the formula:

[Structure: triazole-N—CH$_2$—CH(OC—C(CH$_3$)$_3$)—O—phenyl-X$^1$ (para)]

or a pharmaceutically acceptable non-toxic acid addition salt thereof wherein
  X$^1$ is fluoro, chloro or bromo.

27. A method according to claim 21, wherein the active ingredient is a compound of the formula:

[Structure: triazole-N—CH$_2$—CH(OC—C(CH$_3$)$_3$)—O—phenyl-X$^1$ (para)]

or a pharmaceutically acceptable non-toxic hydrohalic acid salt thereof wherein
  X$^1$ is fluoro, chloro or bromo.

28. A method according to claim 21, wherein the active ingredient is the compound

[Structure: triazole-N—CH$_2$—CH(OC—C(CH$_3$)$_3$)—O—phenyl-Cl (para)]

29. A method according to claim 21, wherein the active ingredient is the compound

[Structure: triazole-N—CH$_2$—CH(OC—C(CH$_3$)$_3$)—O—phenyl-2,4-di-Cl]

30. A method according to claim 21, wherein the active ingredient is the compound

[Structure: triazole-N—CH$_2$—CH(OC—C(CH$_3$)$_3$)—O—phenyl-Br (para)]

31. A method according to claim 21, wherein the active ingredient is the compound

[Structure: triazole-N—CH$_2$—CH(OC—C(CH$_3$)$_3$)—O—phenyl-2,6-di-Cl]

32. A method according to claim 21, wherein the active ingredient is the compound

[Structure: triazole-N—CH$_2$—CH(OC—C(CH$_3$)$_3$)—O—phenyl-Cl (meta)]

33. A method according to claim 21, wherein the active ingredient is the compound

[Structure: triazole-N—CH$_2$—CH(OC—C(CH$_3$)$_3$)—O—phenyl-Cl (ortho)]

34. A method according to claim 21, wherein the active ingredient is the compound

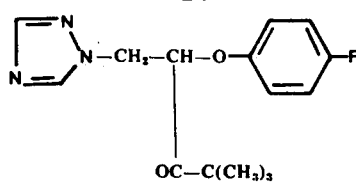

35. A method according to claim 21, wherein the active ingredient is the compound

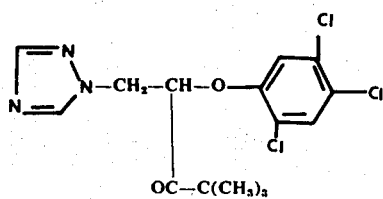

36. A composition according to claim 1 in which the active ingredient is present in the amount of from about 0.1 to 99.5% by weight of the total mixture.

37. A method according to claim 21 wherein the compound is administered in an amount of from about 10 to 30 mg/kg of body weight.

38. A method according to claim 21 in which the active ingredient is administered at a daily dosage of from about 0.5 to 30 g.

39. A method according to claim 21 wherein the compound is in the form of a salt selected from the group consisting of the hydrochloride, hydrobromide, phosphate, nitrate, acetate, maleate, succinate, fumarate, tartrate, citrate, salicylate, sorbate, lactate and naphthalene disulphonate.

40. A method according to claim 39 wherein the salt is the hydrochloride.

41. A method according to claim 21 wherein the administration is oral.

42. A method according to claim 21 wherein the administration is parenteral.

43. A method according to claim 21 wherein the administration is topical.

* * * * *